United States Patent
Heinkel et al.

(10) Patent No.: US 9,459,167 B2
(45) Date of Patent: Oct. 4, 2016

(54) CRANK ARM, CRANKSET, AND POWER MEASURING DEVICE FOR AN AT LEAST PARTIALLY HUMAN POWERED VEHICLE OR TRAINING DEVICE WITH A CRANK DRIVE

(71) Applicant: STORCK BICYCLE GmbH, Idstein (DE)

(72) Inventors: Ulrich Heinkel, Buckenhof (DE); Peter Wolf, Auerbach (DE); Daniel Kriesten, Chemnitz (DE); Stephan Odenwald, Chemnitz (DE); Jens Buder, Chemnitz (DE)

(73) Assignee: Storck Bicycle GmbH, Idstein (DE)

( * ) Notice: Subject to any disclaimer, the term of this patent is extended or adjusted under 35 U.S.C. 154(b) by 0 days.

(21) Appl. No.: 14/081,446

(22) Filed: Nov. 15, 2013

(65) Prior Publication Data
US 2014/0182393 A1   Jul. 3, 2014

(30) Foreign Application Priority Data
Nov. 16, 2012   (DE) ........................ 10 2012 022 447

(51) Int. Cl.
*G01L 5/24* (2006.01)
*G01L 5/13* (2006.01)
(Continued)

(52) U.S. Cl.
CPC  *G01L 5/13* (2013.01); *B62M 3/08* (2013.01); *G01L 1/22* (2013.01); *G01L 3/1457* (2013.01); *G01L 3/242* (2013.01); *A61B 5/221* (2013.01); *Y10T 74/2168* (2015.01)

(58) Field of Classification Search
CPC ....... B62M 3/08; B62M 3/003; G01L 3/242; G01L 5/13; G01L 3/10; G01L 1/22; G01L 3/1457; G01L 3/02; A63B 22/08; A61B 5/221; Y10T 74/2168; B62J 6/18; B62J 2300/002; B60R 16/0307; B60R 16/033; H02K 7/1846; H02K 7/1861
USPC ......................................... 73/862.28, 862.08
See application file for complete search history.

(56) References Cited

U.S. PATENT DOCUMENTS

| | | | | |
|---|---|---|---|---|
| 2009/0119032 A1* | 5/2009 | Meyer | ..................... | G01L 3/242 702/44 |
| 2013/0233091 A1* | 9/2013 | Tetsuka | .................. | B62M 3/003 73/862.621 |

FOREIGN PATENT DOCUMENTS

| | | |
|---|---|---|
| DE | 37 22 728 C1 | 12/1988 |
| DE | 299 24 433 U1 | 6/2003 |

(Continued)

*Primary Examiner* — Lisa Caputo
*Assistant Examiner* — Brandi Hopkins
(74) *Attorney, Agent, or Firm* — Ohlandt, Greeley, Ruggiero & Perle, L.L.P.

(57) ABSTRACT

A power measuring system for an at least partially human powered vehicle or training device with a crank drive, in particular a bicycle, with at least one crank arm of the bicycle being manufactured of fiber-reinforced plastics and the crank arm having a sensor, in particular a strain gage, and with the largest part of the sensor being directly enclosed on all sides by the fiber-reinforced plastics. The force exerted on the respective pedal and from this the torque exerted on the bottom bracket shaft is determined by an electronics unit, which is preferably arranged in a cavity in the bottom bracket shaft, from the signal of sensor. From this, together with the rotational frequency of bottom bracket shaft, which is possibly measured by further sensors or is determined in a calculative way, the power currently generated by the user of the bicycle is determined. The power values can, in particular wirelessly, be sent to a display unit and be displayed thereby in the form of power-related information. The sensors in both crank arms, make it possible to determine the power for the left and the right leg of the cyclist separately.

20 Claims, 2 Drawing Sheets

(51) Int. Cl.
  *B62M 3/08* (2006.01)
  *G01L 3/24* (2006.01)
  *G01L 3/14* (2006.01)
  *G01L 1/22* (2006.01)
  *A61B 5/22* (2006.01)

(56) References Cited

FOREIGN PATENT DOCUMENTS

| WO | 2008/058164 A2 | 5/2008 |
| WO | 2010/000369 A1 | 1/2010 |
| WO | 2010/014242 A1 | 2/2010 |

* cited by examiner

CRANK ARM, CRANKSET, AND POWER MEASURING DEVICE FOR AN AT LEAST PARTIALLY HUMAN POWERED VEHICLE OR TRAINING DEVICE WITH A CRANK DRIVE

BACKGROUND

1. Field of the Disclosure

The present disclosure relates to a crank arm, a crankset, and a power measuring device for an at least partially human powered vehicle or training device with a crank drive.

2. Discussion of the Background Art

By an at least partially human powered vehicle with a crank drive, we understand in particular a common bicycle with a foot pedal crank drive driven by the legs, but also any other at least partially human powered vehicle, in particular a road vehicle, a watercraft or an aircraft, in particular with one or more human powered wheels, which is completely or at least partially driven by the muscles of the user by means of a crank drive, i. e. the propulsion is generated by the rotation of the cranks.

Examples for at least partially human powered vehicles with a crank drive which is not a foot pedal crank drive are bicycles with a hand crank drive, so-called handbikes.

Examples for vehicles which are only partially human powered, are specialized electric bicycles, so-called pedelecs, where an electric motor boosts the pedaling movement of the user in certain riding situations, but cannot completely replace it.

By an at least partially human powered training device with a crank drive, we understand a stationary device for simulating a kind of movement for training purposes which is completely or partially driven by the muscles of the user by means of a crank drive, for example a so-called stationary bicycle for exercising cycling.

The disclosure is described using a bicycle with a common foot pedal crank drive. However, this is not to be understood as a restriction of the usability of the disclosure.

In the field of cycling, both competitive and recreational athletes are interested in recording their current power output. Recording the power output by the cyclist has been established as an inherent part of training supervision and control.

The power generated by the cyclist can be determined from the force exerted on the pedals by the cyclist and the length of the crank arms in connection with the rotational frequency by the physical formula for a rotational movement "power=torque×angular velocity" or "power=torque×2π×rotational frequency".

For determining the force exerted on the pedals, usually sensors are mounted on or in components of the drive train of the bicycle which are located in the drive train as near to the pedals as possible.

In the prior art, in particular sensors at the pedal itself (WO 2010/014242 A1), at the pedal cleat (WO 2010/000369 A1), at the crank spider or at the crank arm (WO 2008/058164 A2), or at the bottom bracket (DE 37 22 728 C1, DE 299 24 433 U1) are mounted for this purpose. Here, the sensors used are usually strain measurement sensors, in particular strain gages, measuring the deformation of the particular component, from which the force exerted on the component can be derived.

The rotational frequency of the crank arms, i. e. the pedaling frequency, can be measured, for instance, as described in WO 2008/058164 A2, by a Hall sensor fixed to the crank spider or to the crank arm in connection with a magnet fixed to the bicycle frame or indirectly by analyzing the force characteristics measured by the force sensor over time.

In one embodiment ("The Crank Arm Approach") of WO 2008/058164 A2, it is suggested to place an arrangement of shear web strain gages in the crank arm. To this end, for example pockets are machined into the front and rear side of the crank arm in order to generate a thin web, and the shear web strain gages are arranged on either side thereof. Alternatively, the strain gages are arranged on an outer surface of the crank arm or on an inner surface of a hollow crank arm.

With the arrangement of the sensor in pockets of the crank arm, the problem arises that the crank arm must extensively be mechanically machined and is at the same time structurally weakened. With the arrangement on an outer surface of the crank arm, the sensor is exposed and is therefore unprotected against impacts from outside like weather conditions or mechanical stress like rubbing against the crank arm with the shoes while riding. Furthermore, the sensor is not hidden from the user, which can adversely affect the look of the crank arm and is therefore not desired for design reasons. With the arrangement on an inner surface of a hollow crank arm, the sensor can only be inserted and fixed with difficulties. Sealing problems with the lead-through of the connection lines of the sensor out of the cavity result, and, in this case as well, the sensor is only partially protected against impacts from outside like, for instance, moisture accumulating in the cavity in the crank arm.

The underlying problem of the present disclosure is therefore to provide a crank arm with a sensor, a crankset with such a crank arm, a power measuring system with such a crankset and a bicycle with such a power measuring system, wherein the sensor is protected better against impacts from outside and wherein the crank arm with the sensor can be manufactured easily and cost-efficiently, and to provide a power measuring and displaying method for such a power measuring system.

SUMMARY

A crank arm in the sense of the disclosure for a bicycle has a fixing device arranged at an outer end of the crank arm, preferably a threaded hole, for fixing a pedal axle of a pedal, a fixing device arranged at an inner and of the crank arm opposite the outer end, for example an opening with a square bore or with a multiple inner serration, for fixing the crank arm to a bottom bracket shaft and a crank arm body extending substantially between the two ends of the crank arm. Here, a detachable or a non-detachable, i. e. a permanent, connection between the crank arm and the bottom bracket shaft can be provided. Here, a pedal in the sense of the disclosure can be a common bicycle pedal for operation by foot, for instance a flat pedal or a clipless pedal, but also—for example with handbikes—a corresponding device for operation by hand.

A crankset in the sense of the disclosure for a bicycle has a left crank arm and a right crank arm as well as a bottom bracket shaft, wherein the left crank arm is fixed to a first end of the bottom bracket shaft by means of the fixing device arranged at its inner end, and the right crank arm is fixed to a second end of the bottom bracket shaft opposite the first end by means of the fixing device arranged at its inner end.

At least one driving element can be fixed to the crankset which is, in the case of a round driving element preferably concentrically to the bottom bracket shaft, arranged at one end of the bottom bracket shaft within the left or the right crank arm. Particularly preferably, the at least one driving element is a chain wheel, but preferably also a tooth belt wheel, a joint for a cardan shaft or the like. Here, the at least one driving element can, for example, be connected by a crank spider formed to the right crank arm to this crank arm, or it can directly be connected to the bottom bracket shaft. For a foot pedal drive of the bicycle, the left and the right crank arms usually extend approximately orthogonally in opposing directions from the bottom bracket shaft, but they can also—for instance in case of a hand drive—extend from the bottom bracket shaft in the same direction.

A power measuring device in the sense of the present disclosure for an at least partially human powered vehicle or training device with a crank drive is an automatic, preferably electronic, device for determining the mechanical power exerted by the user of the vehicle or training device thereon.

A crank arm according to the disclosure comprises at least one first sensor, with the crank arm body of the crank arm being manufactured of fiber-reinforced plastics, and with the largest part of the at least one sensor being directly and on all sides enclosed by the fiber-reinforced plastics.

In the sense of the present disclosure, being "directly enclosed on all sides" shall mean that substantially the complete circumference of the cross-sectional area of the at least one sensor that the sensor has at a certain point is in contact with one or more components of the fiber-reinforced plastics. It is preferred that, with respect to an extension of the at least one first sensor orthogonally to this cross-sectional area, at least 80%, more preferably at least 90%, even more preferably at least 95% of the at least one first sensor are directly and on all sides enclosed by the fiber-reinforced plastics.

In the area which is directly and on all sides enclosed, the sensor and the fiber-reinforced plastics are thus connected at least in a form-fit way and, depending on the chemical properties of the materials involved, possibly also in a materially bonded way.

Areas which are not directly and on all sides enclosed by the fiber-reinforced plastics are, for example, one or more ends of the sensor which serves or serve for electrically connecting the sensor.

The disclosure advantageously connects the material fiber-reinforced plastics, for instance carbon-fiber-reinforced plastics (frequently also called "carbon"), which has already been used and is established in particular in the field of cycling for a long time anyway, with the arrangement of the sensor. By the choice of material and the omission of additional components for fixing or for protecting the sensor, the resulting crank arm is in particular very lightweight.

By fiber-reinforced plastics, we understand a material having at least a matrix material component and a reinforcement fiber component.

Here, the reinforcement fibers preferably consist of organic material like aramid, carbon, polyester, nylon, or polyethylene, or of natural fibers like wood, flax, hemp, or sisal.

The reinforcement fibers used can have different fiber lengths. Preferably, short fibers with a fiber length of 0.1 to 1 mm are used. These reinforcement fibers are in particular advantageous in the case when the component is manufactured by injection molding. More preferably, in particular in combination with a thermoset matrix material, long fibers with a length of 1 mm to 50 mm are used. Particularly preferably, continuous fibers with a length of over 50 mm are used. Continuous fibers are used in particular in the form of rovings or mesh. Fiber-reinforced plastics with continuous fibers fulfills the highest standards in particular with respect to strength and rigidity.

In particular the deformation characteristics and/or the strength of fiber-reinforced plastics can be influenced by the orientation of the reinforcement fibers in the matrix material. Preferably, the reinforcement fibers are oriented in correspondence with known strains, i. e. in the present case preferably parallel to the direction in which the crank arm body extends, which is also the main bending direction during operation.

The matrix material of a fiber-reinforced plastics has as one component preferably a thermoplastic polymer like polyethylene (PE), polyamide (PA), polyetheretherketone (PEEK), polyphenylenesulfide (PPS), polysulfone (PSU), polyetherimide (PEI), or polytetrafluorethene (PTFE), or a thermoset polymer like epoxy resin (EP), unsaturated polyester resin (UP), vinyl ester resin (VE), phenol formaldehyde resin (PF), dialyllphthalate resin (DAP), methacrylate resin (MMA), polyurethane (PUR), or amino resin.

The volume ratio of reinforced fibers to matrix material is preferably adjusted to the expected strain of the crank arm. In particular, a large percentage of longer fibers leads to an increase of rigidity and strength. Preferably, fiber-reinforced plastics has a fiber percentage of 3 to 95 volume %, preferably of 45 to 75 volume %, and particularly preferably from 55 to 65 volume %.

As the fiber-reinforced plastics is usually manufactured from single layers, the rovings or the mesh, which are placed into a mold one after the other during the manufacturing process, the sensor can directly be laid between, i. e. "laminated into", the layers of the crank arm body during the manufacturing process thereof. Here, the sensor is preferably laid below the first two to three fiber layers.

Thus, the sensor is an integral component of the fiber composite of the crank arm body and in this way is particularly well protected against impacts from outside. As the largest part of the sensor is enclosed by the fiber-reinforced plastics on all sides, no problems arise relating to the fixing of the sensor and a possible detachment of the sensor due to vibrations, blows, touches or deformations of the crank arm body or due to impacts by moisture, cleaning agents, heat, light, or other external influences. Furthermore, the sensor is completely hidden from the eyes of the user, and the design of the crank arm is not adversely affected by any recesses, assembly openings, or the like for the sensor.

In a particularly preferred embodiment of the disclosure, the at least one first sensor is a strain measuring sensor. In particular, the at least one first sensor can be a strain gage. This strain gage already changes its electrical resistance as the result of a small strain. In this way, a deformation of the crank arm, from which the force exerted on the crank arm can be deduced, can be measured in a simple way.

In a further particularly preferred embodiment of the disclosure, the at least one first sensor has an elongate form and is stitched onto a two-dimensional carrier material, in particular onto a fiber mesh. In this case, the sensor preferably forms a measuring lattice, and the fiber mesh is the carrier of this measuring lattice.

Here, the sensor preferably has the form of a thread or a wire. The carrier material preferably has the form of a fiber mesh, but can also have the form of a film, a plate, or the like. By stitching, here we understand pulling the elongate sensor several times from one surface of the carrier material to the other, in order to at least preliminarily connect the elongate sensor with the two-dimensional carrier material, so that the carrier material can be arranged together with the elongate sensor in the crank arm according to the disclosure while manufacturing the crank arm.

Here, the carrier material is regarded as part of the fiber-reinforced plastics. In this sense, the enclosure of the sensor on all sides by the fiber-reinforced plastics is not prevented by the contact between the surface of the elongate sensor and the carrier material.

The elongate sensor is preferably arranged on the carrier material in the form of meanderingly reciprocating parallel lines. In this way, the surface of the carrier material can be exploited particularly well. Preferably, hereby a length as large as possible of the elongate sensor is oriented in the same direction, which in turn is preferably oriented in line with the main strain direction of the crank arm, i. e. with the direction of extension of the crank arm body, during the assembly of the sensor. In this case, the strain of the crank arm body can be measured over a particularly great length of the elongate sensor, thus increasing the measurement range.

In a further particularly preferred embodiment of the disclosure, the at least one sensor extends over the complete or approximately over the complete length of the crank arm body. In this way, too, the measurement is done over a particularly great length of the crank arm body, thus again increasing the measurement range.

A crankset for a bicycle according to the disclosure has a left crank arm and a right crank arm, with at least the left crank arm or the right crank arm being a crank arm according to the disclosure. Further, the crankset has a bottom bracket shaft, with the left crank arm being fixed to a first end of the bottom bracket shaft by means of the fixing device arranged at its inner end, and the right crank arm being fixed to a second end of the bottom bracket shaft opposite the first end by means of the fixing device arranged at its inner end. At least one driving element, which (in the case of a round driving element) is arranged concentrically to the bottom bracket shaft at one end of the bottom bracket shaft within a crank arm, can be fixed to the crankset.

The bottom bracket shaft is usually supported against the frame of the bicycle, in particular in a tube-like bottom bracket sleeve, by one or more bearings, preferably rolling bearings. The at least one driving element serves for guiding a transmission element, preferably a chain or a tooth belt, and for transmitting the forces exerted on the pedals and transmitted by the crank arms and the bottom bracket shaft to a driven wheel, usually the rear wheel.

Therefore, in a crankset according to the disclosure, at least one sensor is present in the fiber-reinforced plastics of at least one crank arm as an integral part, without the user being necessarily able to perceive the sensor. Therefore, a crankset according to the disclosure can be sold in a state in which it is already prepared for later retrofitting with a power measuring system.

The crank arm according to the disclosure with the integrated sensor can be manufactured very cost-efficiently, because, apart from the sensor itself and its integration into the fiber-reinforced plastics, hardly any additional components and/or processing steps are necessary when it is manufactured. Furthermore, the weight of the crankset increases only insignificantly due to the integrated sensor, for instance only in the range of one-tenth of a percent. In this way, the user is enabled to buy a crankset prepared in this way without particular disadvantages and for a just slightly higher price, which means that the crankset according to the disclosure can correspondingly be disseminated more widely.

For the manufacturer, this has the advantage that, when marketing a power measuring system which is compatible with the crankset, he can already resort to a large base of bicycles with cranksets prepared for the power measuring system, thus increasing the dissemination of his power measuring system.

Besides a crankset according to the disclosure, a power measuring device according to the disclosure for a bicycle has an electronics unit which is adapted for receiving at least one first sensor signal generated by the at least one first sensor, for processing the at least one first sensor signal to a processed signal and optionally for sending the processed signal to a display unit. The processing of the at least one first sensor signal can—in particular, if the power measuring device has no display unit—also comprise storing the— possibly already preprocessed—at least one first sensor signal.

The electronics unit preferably has an analog/digital converter for converting the analog sensor signal, for instance a measurement current, into a digital signal and an electronic component like a microprocessor or a signal processor for preprocessing and further processing the digitized sensor signal. Furthermore, the electronics unit preferably has a time base, preferably in the form of an oscillating quartz, in order to enable a resolution over time of the analog sensor signal for digitizing and processing it. Finally, the electronics unit preferably has an electric energy storage like a non-rechargeable or a rechargeable battery.

Then the electronics unit can advantageously be retrofitted later at a bicycle which has already been fitted with a crankset according to the disclosure.

Furthermore, the power measuring device according to the disclosure can have a display unit which is adapted for receiving the processed signal from the electronics unit, for post-processing the processed signal to a display signal, and for displaying the display signal in the form of power-related information to the user of the bicycle.

In a preferred embodiment of the disclosure, the bottom bracket shaft has a cavity, and the electronics unit is arranged in the cavity. Since tubular, i. e. hollow bottom bracket shafts are used anyway in particular with modern bicycles for reducing their weight, in many cases this does not make any design modification necessary. With this arrangement of the electronics unit, at the same time the available space is exploited particularly well, and the electronics unit is protected from impacts from outside and cannot be noticed by the user at first glance.

The electronics unit preferably has a housing in the form of a cylindrical capsule or cartridge, for example made of aluminum or plastics, which can be inserted into the hollow bottom bracket shaft from one side. The components of the electronics unit mentioned above are then accommodated in this capsule.

In a further preferred embodiment of the disclosure, the at least one first sensor is connected to the electronics unit by a, in particular multi-core, electric conductor. The electric conductor preferably has the form of a multi-core lace cord, particularly preferably in the form of a ribbon cable. Here, the electric conductor is preferably arranged in the cavity in the bottom bracket shaft, substantially leading to the same advantages as with the arrangement of the electronics unit in the cavity of the bottom bracket shaft.

In the case that both the left and the right crank arms are fitted with a first sensor, it is self-evident that also two electric conductors, each being connected with one first sensor in one of the crank arms, can be provided.

In a further preferred embodiment of the disclosure, the electronics unit is connected to the electric conductor by detachable contacts. This can easily be done by a, in particular multi-polar, plug and a corresponding, in particular multi-polar, socket. Here, the plug can be fixed to the electronics unit, and the socket can be fixed to the bottom bracket shaft or to a crank arm and be connected to the electric conductor, or vice versa.

If there are several first sensors and several electric conductors, the electric conductors are preferably brought together in a single socket or in a single plug with a correspondingly higher number of poles, and the electronics unit preferably still just has a single plug or a single socket, respectively.

The detachable contacts are preferably arranged in such a way that electrical contact between the electronics unit and the electric conductor and thus with the at least one first sensor is automatically established when the electronics unit is inserted into the cavity in the bottom bracket shaft.

In a particularly preferred embodiment of the disclosure, the electronics unit is adapted for wirelessly sending and the display unit for wirelessly receiving the processed signal. In this way, additional wiring at the bicycle induced by the power measuring system, in particular wiring inside the bicycle frame, which would also be difficult to realize as the electronics unit in the bottom bracket shaft is rotating during the operation of the bicycle, becomes superfluous. Here, a well-known and well-established technology of wireless transmission of signals between different components of a bicycle, for instance of the wheel rotation pulses from a magnet sensor at the front fork to a bicycle computer mounted at the handlebar, can be used.

The display unit is preferably an electronic device which is detachably connected to the bicycle or arranged separately from the bicycle, in particular a bicycle computer, a personal digital assistant (PDA), a tablet computer or a mobile phone, in particular a smartphone. In this way, one can make use of the complete functionality available in such a device, for instance of the screen—which is possibly a touch-screen—for displaying power values in the form of text and/or graphics, for entering user commands, for instance for switching the display between the power values for the left and the right leg, for archiving the power-related information or for forwarding the power-related information for analysis at a central site. Such functions offer themselves particularly in the case of deployment in professional cycling.

Besides displaying power-related information to the user of the bicycle during the ride by a display unit connected to the bicycle, it is also possible to display this information to an accompanying person during stationary training by a display unit arranged separately from the bicycle.

As mentioned above, for determining the power generated by the user of the bicycle it is necessary, apart from measuring the force exerted on the pedals, to also determine the rotational frequency of the bottom bracket shaft. This rotational frequency can, as already mentioned as well, be determined by analyzing the measured force characteristics over time, because this force characteristic is in general not constant, but subject to cyclic variations corresponding to the rotations of the cranks. Such a merely calculative determination of the rotational frequency of the bottom bracket shaft requires, however, a sufficiently large computing power in the electronics unit and moreover is subject to a certain uncertainty.

Therefore, in a preferred embodiment of the disclosure, the electronics unit has at least one second sensor and is adapted for jointly processing the at least one first sensor signal and at least one second sensor signal generated by the at least one second sensor to the processed signal.

In a particularly preferred embodiment of the disclosure, the at least one first sensor is a strain measuring sensor, and the electronics unit has at least two second sensors of which a first one is a position sensor for determining the orientation of the bottom bracket shaft, and a second one is an acceleration sensor for determining the angular acceleration of the bottom bracket shaft.

In this embodiment, the electronics unit is on the one hand adapted for determining the torque exerted on the bottom bracket shaft from the at least one first sensor signal. As the measurement value of the first sensor, preferably a strain measurement sensor, has a known relationship to the force exerted on the pedal, the only further information still needed is the length of the crank arm into which the first sensor is integrated. This information can, for instance, be input during the calibration of the power measuring system.

On the other hand, in this embodiment, the electronics unit is adapted for determining the rotational frequency of the bottom bracket shaft from the at least two second sensor signals, i. e. orientation and angular acceleration of the bottom bracket shaft.

In this embodiment, the electronics unit or, if present, the display unit is then adapted for determining the power currently generated by the user of the bicycle.

However, the at least one second sensor can also be arranged separately from the electronics unit at the bicycle, for instance in the form of a pulse generator for the rotation of a wheel which is already available. In this case, the second sensor signal is transmitted separately from the first sensor signals to the electronics unit or, if present, to the display unit, where the joint processing of all first and second sensor signals is then carried out.

The power measuring device according to the disclosure is intended for being used at or with an at least partially human powered vehicle or training device with a crank drive while riding or during stationary operation.

However, the disclosure is not restricted to at least partially human powered vehicles or training devices with a crank drive and can in principle also be used for such vehicles or training devices without a crank drive, for instance for rowing boots or rowing machines. In this case, other force transmission components of the vehicle or training device, for example the oar plates, are then fitted with the at least one first sensor instead of the crank arms.

A method for measuring and for displaying a power generated by a user of a bicycle with a power measuring device according to the disclosure has the following steps:
  generating at least one first sensor signal by the at least one first sensor and transmitting the at least one first sensor signal to the electronics unit
  receiving the at least one first sensor signal by the electronics unit
  processing the at least one first sensor signal by the electronics unit to a processed signal If the power measuring device has a display unit, the method can additionally have the following steps:
  sending the processed signal to the display unit by the electronics unit
  receiving the processed signal by the display unit
  postprocessing the processed signal to a display signal by the display unit
  displaying the display signal to the user of the bicycle in the form of power-related information If the power measuring system has at least one second sensor, the method can additionally have the step of generating at least one second sensor signal by the at least one second sensor. The step of processing the at least one first sensor signal to the processed signal can then additionally also include processing the at least one second sensor signal.

BRIEF DESCRIPTION OF THE DRAWINGS

Further advantages of the disclosure will become clear from the following description in connection with the attached, partially schematic drawings of embodiments of the disclosure. Here, it is shown in FIG. 1: an oblique view of a crankset according to the disclosure (without a chain wheel).

DETAILED DESCRIPTION OF THE PREFERRED EMBODIMENT

Figure 1:
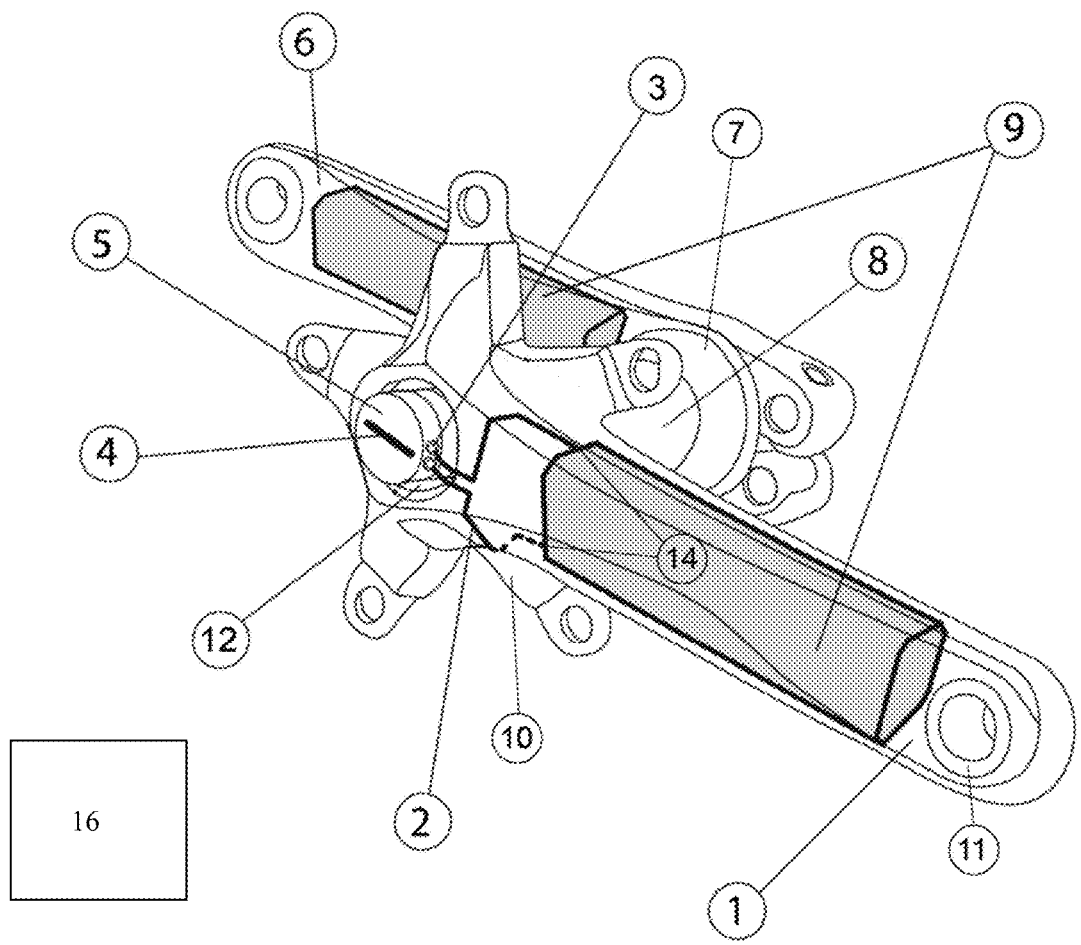

FIG. 1 shows a crankset according to the disclosure from in front obliquely from the right, viewed in the riding direction of the bicycle, with a right crank arm 1 and a left crank arm 6 in a horizontal position. The crank arms 1, 6 are connected by a bottom bracket shaft 8. Bottom bracket 7 is only indicated in the figure by an encapsulated ball bearing.

A crank spider 10 with five radial arms with bores arranged at their ends for fixing one or more chain wheels is integrally shaped to the end of right crank arm 1 near the bottom bracket. Right crank arm 1 is non-detachably connected to the right end of bottom bracket shaft 8, whereas left crank arm 6 is detachably connected to the left end of bottom bracket shaft 8 by means of a clamping.

The bodies of crank arms 1, 6 are made of carbon-fiber-reinforced plastics. Eyelets 11 made of aluminum with inner threads for screwing in the pedal axles are embedded in the ends of the two crank arms 1, 6 near the pedals.

A clamp ring made of aluminum for clamping bottom bracket shaft 8 is also embedded in the end of left crank arm 6 near the bottom bracket. Bottom bracket shaft 8 has the form of a thin-walled tube and is made of aluminum, but it can also be made of other materials like steel, titan or fiber-reinforced plastics.

One strain gage 9 is arranged in each of the two crank arms 1, 6. In the embodiment, strain gage 9 has an electrical resistance of 360Ω. Strain gage 9 has the form of a thin measuring wire which is fixed to a textile thread. In the following, the measuring wire and the textile thread are jointly called a measuring thread.

The measuring thread is stitched onto an approximately rectangular glass fiber mesh (represented in FIG. 1 as a dashed square filled with crosses) by pulling it in short intervals (in the embodiment about 1 mm) in turns from one side of the glass fiber mesh to the other. Here, the measuring thread is stitched onto the glass fiber mesh in the form of lines (FIG. 2), i. e. the measuring thread runs along a long side of the rectangular glass fiber mesh in the form of a first line approximately over the complete length of the glass fiber mesh, changes its direction there, and runs back in parallel to the first line in opposite direction in the form of a second line, is deflected there again and runs in parallel to the second line in the form of a third line in the same direction as the first line again, and so on. In this way, nearly the whole surface of the glass fiber mesh is covered by the measuring thread.

When manufacturing a crank arm 1, 6, the glass fiber mesh stitched with the measuring thread is laminated into the fiber-reinforced plastics of the crank arm body by laying the glass fiber mesh between the mats of carbon-fibers before impregnating it with liquid plastics. Just the ends of the measuring thread are arranged in such a way that they are accessible from outside after manufacturing crank arm 1, 6. In this way, nearly 100% of strain gage 9 are directly enclosed on all sides by the fiber-reinforced plastics.

By specifically forming the shape of the glass fiber mesh and a corresponding arrangement of the lines of the measuring thread, for example in curved paths, it is possible to fit the form of the sensor to the form of the crank arm and thus to achieve a high rate of exploitation of the cross-sectional area of the crank arm by the sensor.

Figure 2:
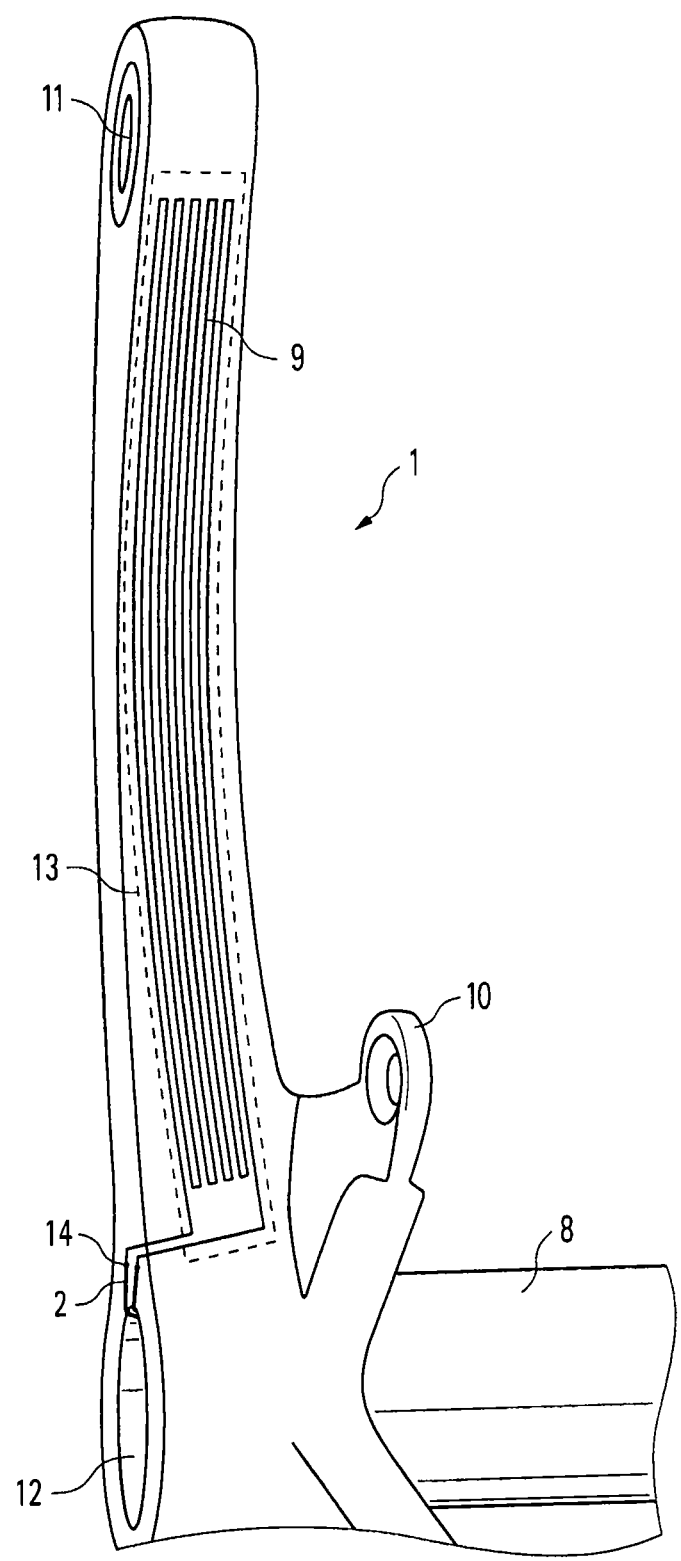
FIG. 2: a top view of a crank arm according to the disclosure with an alternative sensor arrangement.

FIG. 2 shows right crank arm 6 in its highest position from in front, viewed in the riding direction of the bicycle. In the embodiment according to FIG. 2, strain gage 9 is arranged in the crank arm body parallel to the top and bottom side of crank arm 6, i. e. in a plane oriented orthogonally to the plain of rotation of the crank arms, and in this plane covers nearly the complete cross-sectional area of the crank arm body. Here, too, nearly 100% of strain gage 9 are directly enclosed on all sides by the fiber-reinforced plastics.

In FIG. 1, strain gages 9 are integrated into the crank arm bodies of the two crank arms 1, 6 in the same orientation as in FIG. 2, more specifically about in the middle between the top and bottom side of the respective crank arm 1, 6. Here, however, strain gages 9 only extend over a part of the length of the respective crank arm body.

Alternatively, however, strain gage 9 can be arranged in the crank arm body also in parallel to the front and back side of crank arm 6, i. e. in a plane oriented in parallel to the plane of rotation of crank arm 6, and in this plane can cover nearly the complete cross-sectional area of the crank arm body.

In this way, the strain gage is oriented in one of the main strain directions of crank arm 6 during operation of the bicycle and can thus measure the deformation of crank arm 6 with high reliability.

It is also possible to arrange several strain gages 9 in the same crank arm 1, 6 in the same and/or in different orientations.

For instance, two identical strain gages 9 can be arranged symmetrically near the top or the bottom side, respectively, of crank arm 1, 6 and can electrically be connected in parallel in order not to detune the half bridge formed by the sensor.

By a suitable arrangement of several strain gages 9 in the same crank arm 1, 6, the force applied to crank arm 1, 6 can, for example, also be determined separately by its components in tangential and radial direction. This can provide important information for achieving a pedaling movement as uniform as possible, the so-called "smooth pedal stroke", during the training.

The ends of the measuring thread leading out of the fiber composite of the crank arm body are soldered to the ends of a multi-core ribbon cable 2 at a soldering support point 14, with the ribbon cable 2 being guided to an opening of bottom bracket shaft 8 and there being fixed to the inside thereof.

One crank arm or both crank arms 1, 6 are fitted with strain gages 9 in the way described.

If both crank arms 1, 6 are fitted with strain gages 9, the force exerted on the left and on the right pedal and thus the power generated by the left and by the right leg of the cyclist can be distinguished by a suitable analysis of the measuring values provided by strain gages 9, which can be a valuable help for organizing the training in particular in professional cycling. Alternatively, the measuring values of the two crank arms 1, 6 can be used in such a way that they are analyzed in common, yielding a higher precision for the power determined.

The electronics unit 5 has a cylindrical sleeve made of aluminum, which is open at its front side. However, the sleeve can also have a different form and/or be made of a different material like steel or plastics. Inside the sleeve, an electronic circuit board with the electronic components necessary for analyzing and processing the measurement values and transmitting the processed signal is arranged. In particular, a signal amplifier, a signal processor, a storage unit, a sending unit 4 and a rechargeable battery cell are placed on the circuit board. Furthermore, a position sensor, for example a gyroscope, and a single- or multi-axis acceleration sensor, from the measurement values of which the rotational frequency of the bottom bracket shaft can be determined, are placed on the circuit board.

An open front side of the sleeve of the electronics unit 5 can be closed by a lid, for example a plastic lid. Sending unit 4 or its antenna is arranged at the open front side of the sleeve, so that the sleeve and/or the bottom bracket housing do not shield the wireless connection between electronics unit 5 and the display unit 16.

Electronics unit 5 slides from a front side of bottom bracket shaft 8 into the cavity thereof and is clamped or latched there by suitable means. Alternatively, it is also possible to provide an inner thread on the inner surface of bottom bracket shaft 8 and a corresponding outer thread on the outer surface of the sleeve, by which electronics unit 5 can be screwed into bottom bracket shaft 8.

The sleeve has a socket 3 at its outer side which is connected to the circuit board by a cord inside the sleeve. Socket 3 can be arranged, for example, on the cylindrical outer surface or on one of the front faces of the sleeve having the form of circular discs. Socket 3 can have several poles lying side by side or in a circular pattern, or can have poles which are formed as coaxial rings.

Ribbon cable 2 is connected with a plug at its end opposite strain gage 9, which plug is plugged into the socket of the sleeve when mounting electronics unit 5. In the embodiment of FIG. 1, the sleeve of the electronics unit protrudes at the right side of bottom bracket shaft 8 therefrom when it is mounted, so that the plug can be plugged into the two-pole socket 3 arranged on the side face of the sleeve. A plug and a socket 3 which automatically engage when mounting the electronics unit, are preferred, however.

In the electronics unit 5, a power value or two separate power values for the left crank arm 6 and the right crank arm 1, respectively, are determined from the measurement values of strain gages 9, the position and the acceleration sensor, and is sent to a display unit 16 by means of sending unit 4.

Sending unit 4 uses, for example, a standard technology for short range communication like ANT, Bluetooth, Zigbee, or WLAN. This makes it possible to also use a terminal device of a third party supplier like a smartphone as a display unit 16 which terminal device supports the communication technology used and, furthermore, comes with convenient display, analysis, and storage functions. For this purpose, third party suppliers can also develop and offer ready-made software programs, so-called apps, for displaying, analyzing, storing, and managing the power-related information.

LIST OF REFERENCE SIGNS

1 Right crank arm
2 Ribbon cable
3 Socket
4 Sending unit
5 Electronics unit
6 Left crank arm
7 Bottom bracket
8 Bottom bracket shaft
9 Strain gage
10 Crank spider
11 Threaded eyelet for pedal axle
12 Cavity in the bottom bracket shaft
13 Glass fiber mesh
14 Soldering support point
16 Display unit

What is claimed is:

1. A crank arm for an at least partially human powered vehicle or training device with a crank drive, the crank arm having:
    a fixing device arranged at an outer end of the crank arm for fixing a pedal axle of a pedal,
    a fixing device arranged at an inner end of the crank arm opposite the outer end for fixing the crank arm at a bottom bracket shaft,
    a crank arm body extending substantially between the two ends of the crank arm, and
    at least one first sensor,
    wherein the crank arm body is manufactured of fiber-reinforced plastics and that the largest part of the at least one first sensor is directly in contact with, all sides, the fiber-reinforced plastics of the crank arm body.

2. The crank arm according to claim 1, wherein the at least one first sensor is a strain measurement sensor.

3. The crank arm according to claim 1, wherein the at least one first sensor has an elongate form and is stitched onto a two-dimensional carrier material.

4. The crank arm according to claim 1, wherein the at least one first sensor extends over the complete or nearly over the complete length of the crank arm body.

5. The crank arm according to claim 1, wherein said largest part of the at least one first sensor is at least 80%.

6. The crank arm according to claim 1, wherein said largest part of the at least one first sensor is at least 90%.

7. The crank arm according to claim 1, wherein said largest part of the at least one first sensor is at least 95%.

8. A crankset for an at least partially human powered vehicle or training device with a crank drive, comprising:
    a left crank arm and a right crank arm, with at least the left crank arm or the right crank arm being a crank arm according to claim 1, and
    a bottom bracket shaft, with the left crank arm being fixed to a first end of the bottom bracket shaft by said fixing device arranged at its inner end, and with the right crank arm being fixed to a second end of the bottom bracket shaft opposite the first end by the fixing device arranged at its inner end.

9. A power measuring device for an at least partially human powered vehicle or training device with a crank drive, comprising:
    a crankset according to claim 8, and
    an electronics unit which is adapted for receiving at least one first sensor signal generated by the at least one first sensor, for processing the at least one first sensor signal to a processed signal.

10. The power measuring device according to claim 9, wherein the bottom bracket shaft has a cavity and the electronics unit is arranged in the cavity.

11. The power measuring device according to claim 10, wherein the at least one first sensor is connected to the electronics unit by an electrical conductor which is guided in the cavity in the bottom bracket shaft.

12. The power measuring device according to claim 11, wherein the electronics unit is detachably connected to the electrical conductor by detachable contacts.

13. The power measuring device according to claim 9, wherein the power measuring device has a display unit, and the electronics unit is adapted for wirelessly sending and the display unit for wirelessly receiving the processed signal.

14. The power measuring device according to claim 9, wherein the power measuring device has a display unit, and the display unit is an electronic device which is detachably connected to the at least partially human powered vehicle or training device or is arranged separately therefrom.

15. The power measuring device according to claim 9, wherein the electronics unit has at least one second sensor and is adapted for jointly processing the at least one first sensor signal and at least one second sensor signal generated by the at least one second sensor to the processed signal.

16. The power measuring device according to claim 9, wherein the at least one first sensor is a strain measuring sensor,
   the electronics unit has at least two second sensors, a first one of which is a position sensor and a second one is an acceleration sensor,
   that the electronics unit is adapted for determining the torque exerted on the bottom bracket shaft from the at least one first sensor signal and for determining the rotational frequency of the bottom bracket shaft from the at least two second sensor signals
   and that the electronics unit or, if the power measurement device has a display unit, the display unit is adapted for determining the power currently generated by the user of the at least partially human power vehicle or training device.

17. At least partially human powered vehicle or training device with a crank drive with a power measurement device according to claim 9.

18. The power measuring device according to claim 9, further comprising a display unit adapted for receiving the processed signal from the electronics unit, for postprocessing the processed signal to a display signal, and for displaying the display signal in the form of power-related information to the user of the at least partially human powered vehicle or training device.

19. The method according to claim 9, further comprising:
   generating at least one second sensor signal by at least one second sensor in the electronics unit,
   processing the at least one first and the at least one second sensor signal by the electronics unit to the processed signal,
   sending the processed signal to the display unit by the electronics unit,
   receiving the processed signal by the display unit,
   postprocessing the processed signal to a display signal by the display unit, and
   displaying the display signal to the user of the at least partially human powered vehicle or training device in the form of power-related information.

20. A method for measuring and for displaying a power generated by a user of an at least partially human powered vehicle or training device with a crank drive with a power measuring device according to claim 9, comprising:
   generating at least one first sensor signal by the at least one first sensor and transmitting the at least one first sensor signal to the electronics unit, and
   receiving the at least one first sensor signal by the electronics unit.

* * * * *